United States Patent
Nagashima et al.

(10) Patent No.: US 9,730,971 B2
(45) Date of Patent: Aug. 15, 2017

(54) FEED FOR PREVENTING AND/OR TREATING DISEASES CAUSED BY CLOSTRIDIUM BACTERIUM IN LIVESTOCK, AND AGENT AGAINST CLOSTRIDIUM

(75) Inventors: Kyo Nagashima, Sodegaura (JP); Masami Mochizuki, Sodegaura (JP); Yasuaki Sugimoto, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1213 days.

(21) Appl. No.: 13/139,127

(22) PCT Filed: Dec. 14, 2009

(86) PCT No.: PCT/JP2009/070829
§ 371 (c)(1),
(2), (4) Date: Jun. 10, 2011

(87) PCT Pub. No.: WO2010/067883
PCT Pub. Date: Jun. 17, 2010

(65) Prior Publication Data
US 2011/0250303 A1   Oct. 13, 2011

(30) Foreign Application Priority Data

Dec. 12, 2008 (JP) ................................. 2008-317425

(51) Int. Cl.
| | | |
|---|---|---|
| A61K 36/22 | (2006.01) |
| A61K 31/05 | (2006.01) |
| A61K 31/60 | (2006.01) |
| A23K 20/111 | (2016.01) |
| A23K 20/158 | (2016.01) |
| A23K 20/10 | (2016.01) |
| A23K 50/10 | (2016.01) |
| A23K 50/75 | (2016.01) |
| A23K 50/30 | (2016.01) |

(52) U.S. Cl.
CPC .............. *A61K 36/22* (2013.01); *A23K 20/10* (2016.05); *A23K 20/111* (2016.05); *A23K 20/158* (2016.05); *A23K 50/10* (2016.05); *A23K 50/30* (2016.05); *A23K 50/75* (2016.05); *A61K 31/05* (2013.01); *A61K 31/60* (2013.01)

(58) Field of Classification Search
None
See application file for complete search history.

(56) References Cited

U.S. PATENT DOCUMENTS

| | | | | |
|---|---|---|---|---|
| 5,725,894 A * | 3/1998 | Toyomizu et al. | ........... | 426/2 |
| 6,379,694 B1 | 4/2002 | Hatano et al. | | |
| 2003/0157159 A1* | 8/2003 | Franklin et al. | ........... | 424/450 |
| 2008/0226760 A1* | 9/2008 | Torrent Campmany | ...... | 424/776 |

| | | | |
|---|---|---|---|
| 2010/0183755 A1 | 7/2010 | Kobayashi et al. | |
| 2010/0183756 A1 | 7/2010 | Kobayashi et al. | |
| 2011/0177184 A1 | 7/2011 | Suzuki et al. | |

FOREIGN PATENT DOCUMENTS

| | | |
|---|---|---|
| JP | 1-172341 A | 7/1989 |
| JP | 3 240721 | 10/1991 |
| JP | 8-231410 A | 9/1996 |
| JP | 2001 151675 | 6/2001 |
| WO | 2008 149994 | 12/2008 |
| WO | 2009/139468 | 11/2009 |

OTHER PUBLICATIONS

Clostridium. "Office of Public Health". Web Publication Date: Dec. 21, 2006 [Retrieved from the Internet on: Jul. 16, 2015]. Retrieved from: <URL: http://dhh.louisiana.gov/assets/oph/Center-PHCH/Center-CH/infectious-epi/EpiManual/ClostridiumManual.pdf>.*
"Botulism". CDC. Retrieved from the Internet on: Jul. 16, 2015. Retrieved from: <URL:http://www.cdc.gov/nczved/divisions/dfbmd/diseases/botulism/>.*
"Current Treatments and Future Directions". Retrieved from the Internet on: Jul. 16, 2015. Retrieved from: <URL: http://www.bio.davidson.edu/people/sosarafova/assets/bio307/cahermes/treatment.htm>.*
Smart et al. Journul of Applied Bacteriology 1983, 54, 135-139.*
Watanabe, Y., et al., "Search of a Monesin Substituent Substance, Influence of Cashew Nut Shell Liquid on Rumen Farmentation," The Japanese Society Zootechnical Science Annual Meeting, Abstracts, p. 18, I27-15, (Mar. 27, 2008) (with English translation).
Akinpelu, D.A., "Antimicrobial activity of *Anacardium occidentale* bark," Fitoterapia, vol. 72, pp. 286-287, (2001).
Eichbaum, F.W., "Biological properties of ana-cardic acid (0-pentadecadienyl-salicylic acid) and related compounds.. I. General discussion. Bactericidal action. II. Anti-enzymatic action of anacardic acid and its derivatives. III. Antifebrile action of anacardic acid and its derivatives. IV. The vermicidal, antiprotozoic, antiecto-parasitic and larvicidal action of anacardates. V. Toxicology of anacardic acid and related compounds.," MEM Inst Butantan, vol. 19, pp. 71-133, (1946) (English Abstract only).
International Search Report issued Mar. 16, 2010 in PCT/JP09/070829 filed Dec. 14, 2009.
U.S. Appl. No. 13/376,965, filed Dec. 8, 2011, Mochizuki, et al.
Masaki Himejima et al., "Antibacterial Agents from the Cashew Anacardium Occidentale (Anacardiaceae) Nut Shell Oil", J. Agric. Food Chem., vol. 39, No. 2, 1991, pp. 418-421.
Extended European Search Report issued Feb. 8, 2013 in European Patent Application No. 09831986.6.
Isao Kubo, et al., "Structure-Antibacterial Activity Relationships of Anacardic Acids", Journal of Agriculture & Food Chemistry, vol. 41, No. 6, XP000369580, 1993, pp. 1016-1019.

(Continued)

Primary Examiner — Terry A McKelvey
Assistant Examiner — Catheryne Chen
(74) Attorney, Agent, or Firm — Oblon, McClelland, Maier & Neustadt, L.L.P.

(57) ABSTRACT

The present invention provides a controlling agent for a disease caused by a *Clostridium* bacterium, comprising a cashew nut shell liquid, a heat-treated cashew nut shell liquid, anacardic acid, cardanol, or anacardic acid and cardanol.

15 Claims, No Drawings

(56) References Cited

OTHER PUBLICATIONS

Hisae Muroi, et al., "Synergistic effects of anacardic acids and methicillin against methicillin resistant *Staphylococcus aureus*", Bioorganic & Medicinal Chemistry, vol. 12, XP055051385, 2004, pp. 583-587.
New Zealand Examination Report issued Jan. 23, 2013, in Patent Application No. 606076.
Office Action dated Nov. 19, 2013 in Japanese Patent Application No. 2010-542146 (with partial English language translation).
Masaaki Toyomizu, et al, "Inhibitory effect of dietary anacardic acid supplementation on cecal lesion formation following chicken coccidial infection" Animal Science Journal, vol. 74, No. 2, 2003, pp. 105-109.
Indian Office Action dated Jun. 12, 2017 in connection with corresponding Indian Patent Application No. 4866/CHENP/2011.

* cited by examiner

FEED FOR PREVENTING AND/OR TREATING DISEASES CAUSED BY CLOSTRIDIUM BACTERIUM IN LIVESTOCK, AND AGENT AGAINST CLOSTRIDIUM

TECHNICAL FIELD

The present invention relates to a controlling agent for a disease caused by a *Clostridium* bacterium, the controlling agent comprising a cashew nut shell liquid, a heat-treated cashew nut shell liquid, anacardic acid, cardanol, or anacardic acid and cardanol.

BACKGROUND ART

Infectious diseases of livestock cause a reduction in the body weight of the domestic animal or cause various symptoms, and as a result, the value of the domestic animal as a product is remarkably reduced. For example, *Staphylococcus aureus* is a bacterium causing mastitis, subcutaneous tumor, and pyemia in cattle, sheep, and goats, rash in horses, arthritis, dermatitis, and sepsis in pigs and chickens. Meanwhile, *Streptococcus suis* is a bacterium causing meningitis, sepsis, endocarditis, and arthritis in pigs.

In addition, of *Clostridium* bacteria, *Clostridium perfringens* causes necrotic enteritis through its infection and causes enterotoxemia and malignant edema. Necrotic enteritis exhibits both high morbidity and high fatality, and hence, the disease gives great economical damage to the industries of poultry raising, broiler farming, pig farming, and dairy. Thus, of many diseases of livestock and domestic fowls, necrotic enteritis is one of the most important diseases, for which the controlling measure must be rapidly established.

The features of necrotic enteritis include diarrhea in piglets and chicks clinically, and involve invasion of a bacterium into the intestinal mucosa and necrosis of the small intestine. Enterotoxemia is a disease in which *Clostridium perfringens* grows in the small intestine of an animal and produces a toxin, and the toxin causes a necrotic and hemorrhagic lesion, resulting in acute death because of toxemia. Malignant edema is a disease in which a bacterium enters a wound surface produced accidentally or by surgery to develop the disease, and the bacterium germinates, reproduces, and generates a toxin, causing toxemia and bacteremia and finally leading to death.

*Clostridium perfringens* infectious disease is a serious infectious disease, but methods for its prevention and therapy have not yet been established. For example, suitable farming and controlling have been performed as a preventive method, but actually, the prevention is extremely difficult.

In order to prevent and treat *Clostridium perfringens* infectious disease, a method comprising administering an antibiotic and any other antimicrobial agent with a feed has also been conducted. However, in particular, such problems as occurrence of resistant bacteria and persistence of antibiotics and the like in meat have occurred in recent years, and hence, there is a growing tendency that administering antibiotics and the like to animals is not proper. Thus, it has been desired to develop a method for preventing and treating this disease without using antibiotics and the like, and a medicament.

Meanwhile, there has been known a medicament for preventing and treating a *Clostridium perfringens* infectious disease of livestock and domestic fowls, the medicament containing one kind or two or more kinds of herbal medicine selected from the group consisting of *Phellodendri cortex, Geranium thunbergii, Magnolia obovata, Salvia miltiorrhiza bunge, Anemarrhena rhizome, Rheum, Syzygium aromaticum, Ligustrum lucidum Ait, Schizonepeta tenuifolia, Cinnamomi cortex, Scrophularia ningpoensis, Cassiae semen, Eriobotryae folium, Saposhnikovia seseloides, Humulus lupulus, Perilla herb, Myrica rubra, Forsythia suspensa*, Aloe, ox bile, *Clematis chinensis* Osbeck, *Prunus mume* Sieb. Et Zucc., *Rabdosia japonica, Plantago asiatica, Magnolia kobus, Artemisia capillaris* thunb, *Aquilaria agallocha, Cnidium officinale, Ligusticum sinense* oliv, *Rhus chinensis, Cornus officinalis, Lithospermum erythrorhizon, Picrorhiza scrophulariiflora, Paeonia lactiflora, Rosa laevigata* Michx, thyme, *Nandina domestica* var. leucocarpa, *Sanguisorba officinalis*, and *Ephedra* (Patent Literature 1). In addition, there has been known a medicament for preventing and treating *clostridium perfringens* infectious disease characterized by containing pinene, thymol, eugenol, limonene, *myristica fragrans*, thyme, *syzygium aromaticum*, and citrus (Patent Literature 2).

However, there remains a problem that the effect of those techniques is not constant, and consequently, the techniques have not been put into practice.

It is known that a cashew nut shell liquid and/or anacardic acid have/has an antimicrobial action (Non Patent Literature 1) and a coccidiosis-alleviating action (Patent Literature 3). In addition, in has been reported that a cashew nut shell liquid and/or anacardic acid have/has an antimicrobial action against Gram-positive bacteria such as *Staphylococcos aureus, Streptococcus mutans, Bacillus subtilis*, and *Bacillus ammoniagenes*, and have/has no antimicrobial action against Gram-negative bacteria such as *Escherichia coli, Enterobacter aerogenes*, and *Pseudomonas aeruginosa* and fungi such as *Saccharomyces cerevisiae, Candida utilis*, and *Penichillium chrysogenum* (Non Patent Literature 2). However, it has not been known that a cashew nutshell liquid and/or anacardic acid have/has an antimicrobial action against *Clostridium* bacteria, particularly against *Clostridium perfringens*, and there have been no reports on effects of preventing and treating necrotic enteritis, enterotoxemia, and malignant edema.

PRIOR ART DOCUMENTS

Patent Document

Patent Document 1: JP 2599161 B
Patent Document 2: JP 2008-110951 A
Patent Document 3: JP 08-231410 A

Non Patent Document

Non Patent Document 1: Muroi, H. et al. Bioorganic & Medicinal Chemistry 12, 583-587 (2004)
Non Patent Document 2: Himejima M. and Kudo I., J. Agric. Food Chem., 39, 418-421 (1991)

SUMMARY OF THE INVENTION

An object of the present invention is to control *Clostridium perfringens* infectious disease, which is a serious infectious disease of livestock.

The inventors of the present application have intensively studied to solve the above-mentioned problems. As a result, the inventors have found that a cashew nut shell liquid, a heat-treated cashew nut shell liquid, anacardic acid, cardanol, or anacardic acid and cardanol can be used for controlling a disease caused by *Clostridium perfringens*. Thus, the present invention has been completed.

That is, the summary of the present invention is as below.

(1) A controlling agent for a disease caused by a *Clostridium* bacterium, comprising a cashew nut shell liquid, a heat-treated cashew nut shell liquid, anacardic acid, cardanol, or anacardic acid and cardanol.

(2) A composition for a feed for controlling a disease caused by a *Clostridium* bacterium, comprising a cashew nut shell liquid, a heat-treated cashew nut shell liquid, anacardic acid, cardanol, or anacardic acid and cardanol.

(3) A feed for controlling a disease caused by a *Clostridium* bacterium, comprising a cashew nut shell liquid, a heat-treated cashew nut shell liquid, anacardic acid, cardanol, or anacardic acid and cardanol.

(4) A composition for a feed for controlling a disease caused by a *Clostridium* bacterium, comprising the controlling agent for a disease caused by a *Clostridium* bacterium according to (1).

(5) A feed for controlling a disease caused by a *Clostridium* bacterium, comprising the composition for a feed for controlling a disease caused by a *Clostridium* bacterium according to (4).

(6) A method of controlling a disease caused by a *Clostridium* bacterium, comprising administering a cashew nut shell liquid, a heat-treated cashew nut shell liquid, anacardic acid, cardanol, or anacardic acid and cardanol to livestock in which the disease caused by a *Clostridium* bacterium is developed.

(7) A cashew nut shell liquid, a heat-treated cashew nut shell liquid, anacardic acid, cardanol, or anacardic acid and cardanol for use in producing a controlling agent for a disease caused by a *Clostridium* bacterium.

(8) A cashew nut shell liquid, a heat-treated cashew nut shell liquid, anacardic acid, cardanol, or anacardic acid and cardanol for use in producing a composition for a feed for controlling a disease caused by a *Clostridium* bacterium.

(9) A cashew nut shell liquid, a heat-treated cashew nut shell liquid, anacardic acid, cardanol, or anacardic acid and cardanol for use in producing a feed for controlling a disease caused by a *Clostridium* bacterium.

The controlling agent and the feed containing the agent of the present invention are capable of controlling a disease caused by a *Clostridium* bacterium by being administered to livestock.

The controlling agent and the feed containing the agent of the present invention are capable of killing *Clostridium* bacteria to improve intestinal environment, thereby promoting the growth of livestock.

BEST MODE FOR CARRYING OUT THE INVENTION

The controlling agent for a disease caused by a *Clostridium* bacterium of the present invention comprises a cashew nut shell liquid, a heat-treated cashew nut shell liquid, anacardic acid, cardanol, or anacardic acid and cardanol. In the present invention, control includes both prevention and therapy.

The cashew nut shell liquid to be used in the present invention is an oily liquid contained in the shell of the seed of a cashew nut tree (*Anacardium occidentale* L.). The cashew nut shell liquid contains, as the components thereof, anacardic acid, cardanol, and cardol. Anacardic acid is generally converted into cardanol by heat treatment. Heat-treated cashew nut shell liquid which contains cardanol and cardol only can be used.

Non-heat treated cashew nut shell liquid extracted by compressing cashew nut shells (hereinafter referred to as cashew nut shell liquid) contains 55 to 80 mass % of anacardic acid, 5 to 20 mass % of cardanol, and 5 to 30 mass % of cardol as described in J. Agric. Food Chem. 2001, 49, 2548-2551.

Heat-treated cashew nut shell liquid obtained by heat treating a cashew nut shell liquid at 130° C. or above, wherein most part of anacardic acid which is the main component of cashew nut shell liquid is decarboxylated to convert to cardanol, contains 0 to 10 mass % of anacardic acid, 55 to 80 mass % of cardanol, and 5 to 30 mass % of cardol.

The cashew nut shell liquid used in the present invention can be obtained as a vegetable oil extracted by compressing the shell of a cashew nut. Further, the cashew nut shell liquid used in the present invention can also be obtained by heating or extracting, e.g., dry-distilling or solvent-extracting a cashew nut shell. In addition, the cashew nut shell liquid used in the present invention can be obtained according to a method described in JP 08-231410 A.

The cashew nut shell liquid used in the present invention may also be a liquid obtained by pulverizing/crushing the shell of a cashew nut without heating. Further, the shell itself may be used.

For the cashew nut shell liquid used in the present invention, a commercially-available product may also be used.

The cashew nut shell liquid of the present invention can be the heat-treated cashew nut shell liquid obtained by heat treating the cashew nut shell liquid obtained as mentioned above at 70° C. or above, preferably at 130° C. or above.

The cashew nut shell liquid of the present invention can be obtained by compressing and extracting the cashew nut shell and heat treating them at 130° C.

The controlling agent for a disease caused by a *Clostridium* bacterium of the present invention can contain a heat-treated cashew nut shell liquid, anacardic acid, cardanol, or anacardic acid and cardanol instead of a cashew nut shell liquid.

As anacardic acid used in the present invention, there are exemplified natural anacardic acid, synthetic anacardic acid, and the derivatives thereof. Further, commercially-available anacardic acid may be used. As described in JP 08-231410 A, anacardic acid may be obtained, for example, by eluting the cashew nut shell liquid, which has been obtained by subjecting the cashew nut shell to extraction treatment with an organic solvent, through chromatography on a silica gel column using a solvent of n-hexane, ethyl acetate, and acetic acid mixed at varied ratios (JP 03-240721 A, JP 03-240716 A, and the like).

As cardanol used in the present invention, there are exemplified natural cardanol, synthetic cardanol, and the derivatives thereof. Cardanol to be used in the present invention can be obtained by decarboxylating anacardic acid which is main component of a cashew nut shell liquid.

When a heat-treated cashew nut shell liquid is used, a preferable ration of anacardic acid:cardanol in the heat-treated cashew nut shell liquid is 0:100 to 20:80.

The content of a cashew nut shell liquid, a heat-treated cashew nut shell liquid, anacardic acid, cardanol, or anacardic acid and cardanol in the controlling agent for a disease caused by a *Clostridium* bacterium of the present invention is, on the basis of the total amount of the controlling agent, preferably 1 mass % to 100 mass %, more preferably 5 mass % to 95 mass %, and particularly preferably 10 mass % to 90 mass %. When the content is 1 mass % or more, it can be expected that a disease caused by a *Clostridium* bacterium can be effectively controlled. The tendency is remarkable when the content is 5 mass % or more and particularly preferably 10 mass % or more, which is preferred. On the other hand, although a disease caused by a *Clostridium* bacterium can be controlled even when the content is 100 mass %, the content is preferably 95% or less and particularly preferably 90% or less for improving palatability of the animal.

The controlling agent of the present invention can be used for controlling a disease caused by a *Clostridium* bacterium.

In the present invention, the phase "disease caused by a *Clostridium* bacterium" refers to a disease developed particularly because of the infection of *Clostridium perfringens*. Specific examples of the disease include, but are not limited to, necrotic enteritis, enterotoxemia, and malignant edema.

Examples of the *Clostridium* bacteria contained in the present invention include, but are not limited to, *Clostridium perfringens, C. tetani, C. botulinum, C. difficile, C. thermocellum,* and *C. butyricum.*

The controlling agent for a disease caused by a *Clostridium* bacterium of the present invention may contain, in addition to a cashew nut shell liquid, a heat-treated cashew nut shell liquid, anacardic acid, cardanol, or anacardic acid and cardanol, any excipient as long as the excipient can be used for a feed, a drug, or a food product, such as lactose, saccharose, D-mannitol, starch, corn starch, crystalline cellulose, silica gel, and light anhydrous silicic acid.

The controlling agent for a disease caused by a *Clostridium* bacterium of the present invention may further contain, in addition to a cashew nut shell liquid, a heat-treated cashew nut shell liquid, anacardic acid, cardanol, or anacardic acid and cardanol, an arbitrary component(s) such as a component which is effective for the growth promotion of livestock and domestic fowls, a nutritional supplement component, a component for enhancing the preservation stability, or a coating component. Examples of the arbitrary components include raw materials for a feed, a feed additive, raw materials for a food and a food additive, and raw materials for a medicine. For example, the followings are included: probiotics such as *Enterococcus, Bacillus, Bifidus* and *Lactobacillus*; enzymes such as amylase and lipase; vitamins such as L-ascorbic acid, choline chloride, inositol, and folate; minerals such as potassium chloride, iron citrate, magnesium oxide, and phosphates; amino acids such as DL-alanine, DL-methionine, L-lysine; organic acids such as fumaric acid, butyric acid, lactic acid, acetic acid, and their salts; antioxidants such as ethoxyquin and dibutylhydroxytoluene; fungicides such as calcium propionate; binders such as carboxylmethyl cellurose (CMC), casein sodium, and sodium polyacrylate; emulsifiers such as glycerin fatty acid ester and sorbitan fatty acid ester; pigments such as astaxanthin and canthaxanthin; and flavoring agents such as various esters, ethers, and ketones.

The dosage form of the controlling agent for a disease caused by a *Clostridium* bacterium of the present invention is not particularly limited, and the agent may be in an arbitrary form such as a powder formulation, a liquid formulation, a solid, a tablet, a capsule, an emulsion, a pellet, and a coated formulation, and preferred are a powder formulation, a liquid formulation, a capsule, a pellet, and a coated formulation.

The powder formulation may be obtained by adding the excipient to the cashew nut shell liquid, the heat-treated cashew nut shell liquid, anacardic acid, cardanol, or anacardic acid and cardanol and forming the mixture into powder.

As the liquid formulation, the cashew nut shell liquid, the heat-treated cashew nut shell liquid, anacardic acid, cardanol, or anacardic acid and cardanol may be used as it is, the cashew nut shell liquid, the heat-treated cashew nut shell liquid, anacardic acid, cardanol, or anacardic acid and cardanol may be dissolved in a solvent such as ethanol, or the cashew nut shell liquid, the heat-treated cashew nut shell liquid, anacardic acid, cardanol, or anacardic acid and cardanol may be used after the excipient or an arbitrary component is added.

The capsule may be obtained by filling the cashew nut shell liquid, the heat-treated cashew nut shell liquid, anacardic acid, cardanol, or anacardic acid and cardanol into a capsule as it is, or by adding the excipient or an arbitrary component thereto.

The pellet may be obtained by adding the excipient to the cashew nut shell liquid, the heat-treated cashew nut shell liquid, anacardic acid, cardanol, or anacardic acid and cardanol, and granulating and pelletizing the mixture.

The coated formulation may be obtained by adding the excipient to the cashew nut shell liquid, the heat-treated cashew nut shell liquid, anacardic acid, cardanol, or anacardic acid and cardanol, granulating the mixture, and coating the resultant with a coating agent or the like.

As described above, the controlling agent for a disease caused by a *Clostridium* bacterium of the present invention can be produced by mixing the cashew nut shell liquid, the heat-treated cashew nut shell liquid, anacardic acid, cardanol, or anacardic acid and cardanol with, if necessary, an excipient or an arbitrary component and formulating the mixture. Note that, depending on the form of the formulation, the above-mentioned pulverized/crushed product of the cashew nut shell or the cashew nut shell as it is without being subjected to any treatment is mixed with another arbitrary component(s), and the mixture can be used as the controlling agent of the present invention. In addition, without being mixed with another arbitrary component(s), the pulverized/crushed product as it is or the cashew nut shell as it is may be used as the controlling agent, and the controlling agent as it is may also be used as a composition for a feed or a feed. Further, the cashew nut shell liquid, the heat-treated cashew nut shell liquid, anacardic acid, cardanol, or anacardic acid and cardanol are dissolved in a solvent such as ethanol and the resultant can be mixed and absorbed to a composition for a feed or a feed.

The composition for a feed of the present invention comprises a cashew nut shell liquid, a heat-treated cashew nut shell liquid, anacardic acid, cardanol, or anacardic acid and cardanol. The content of the cashew nut shell liquid, the heat-treated cashew nut shell liquid, anacardic acid, cardanol, or anacardic acid and cardanol in the composition for a feed of the present invention is, on the basis of the total amount, preferably 0.0005 mass % to 100 mass %, more preferably 0.05 to 95 mass %, and particularly preferably 1 to 90 mass %. When the content is 0.0005 mass % or more, it can be expected that the disease caused by a *Clostridium* bacterium can be controlled effectively. The tendency is remarkable when the content is 0.05 mass % or more and particularly preferably 1 mass % or more, which is preferred. On the other hand, although the disease caused by a *Clostridium* bacterium can be controlled even when the content is 100 mass %, the content is preferably 95% or less and particularly preferably 90% or less for improving palatability of the animal.

In the case where the controlling agent for a disease caused by a *Clostridium* bacterium of the present invention is used as a composition for a feed, the controlling agent is mixed with another supplement component used in supplements for animals (hereinafter referred to as supplement) and may be used as a supplement. The kind of the supplement and the components other than the cashew nut shell liquid, the heat-treated cashew nut shell liquid, anacardic acid, cardanol, or anacardic acid and cardanol are not particularly limited.

The feed of the present invention comprises a cashew nut shell liquid, a heat-treated cashew nut shell liquid, anacardic acid, cardanol, or anacardic acid and cardanol.

Note that the content of the cashew nut shell liquid, the heat-treated cashew nut shell liquid, anacardic acid, cardanol, or anacardic acid and cardanol in the feed of the present invention is, on the basis of the total amount, preferably 0.001 to 5 mass %, more preferably 0.01 to 2 mass %, and particularly preferably 0.1 to 1 mass % with respect to a dry mass of the feed. When the content is 0.001 mass % or more, it can be expected that the disease caused by a *Clostridium* bacterium can be controlled effectively. The tendency is remarkable when the content is 0.01 mass % or more and particularly preferably 0.1 mass % or more, which is preferred. On the other hand, although the disease caused by a *Clostridium* bacterium can be controlled even when the content is 5 mass % or less, the content is preferably 2 mass % or less and particularly preferably 1 mass % or less for improving palatability of the animal.

The feed of the present invention can be produced by adding a cashew nut shell liquid, a heat-treated cashew nut shell liquid, anacardic acid, cardanol, or anacardic acid and cardanol as it is, or a composition for a feed comprising a cashew nut shell liquid, a heat-treated cashew nut shell liquid, anacardic acid, cardanol, or anacardic acid and cardanol to a feed component and mixing the resultant. On this occasion, when a powdery or solid feed composition is used, the form of the feed composition may be modified into liquid form or gel form for the purpose of facilitating the mixing process. In this case, the following may be used as a liquid carrier: water; a vegetable oil; a liquid animal oil; a mineral oil; a synthetic oil; and fluid such as a water-soluble polymer compound. Further, in order to keep the uniformity of the cashew nut shell liquid, the heat-treated cashew nut shell liquid, anacardic acid, cardanol, or anacardic acid and cardanol in the feed, the feed preferably contains alginic acid, sodium alginate, a xanthan gum, casein sodium, an arabic rubber, a guar gum, or a water-soluble polysaccharide such as tamarind seed polysaccharide.

The species of animals that ingest the feed of the present invention includes livestock such as cows and pigs and domestic fowls such as chickens. The amount of feed ingested by an animal may be appropriately adjusted depending on the animal's species, body weight, age, sex, health condition, feed component, etc.

Any method usually used may be adopted as a method of feeding animals and a method of breeding animals depending on the species of animals.

EXAMPLES

Production Example 500 kg of cashew nut shells were obtained from Cashew Trading Co., Ltd., and the shells were compressed, to thereby produce 158 kg of cashew nut shell liquid (CNSL). Heat-treated cashew nut shell liquid (Cold Press Oil made in India) wherein anacardic acid was converted into cardanol by heat treatment at 130° C. was obtained from Cashew Trading Co., Ltd.

The composition of cashew nut shell liquid was measured as follows. That is, HPLC (Waters600, Nihon Waters K.K.), detector (Waters490E, Nihon Waters K.K.), printer (Chromatopack C-R6A, Simadzu Co.), and columns (SUPELCO-SIL LC18, SUPELCO Inc.) were used. A solvent of acetonitrile:water:acetic acid in 80:20:1 (volume ratio) was used and the flow rate was 2 ml/minute. The absorbance was detected at 280 nm.

The composition of cashew nut shell liquid was 61.8 mass % of anacardic acid, 8.2 mass % of cardanol, and 19.9 mass % of cardol. The composition of heat-treated cashew nut shell liquid was 0.0 mass % of anacardic acid, 71.4 mass % of cardanol, and 14.4 mass % of cardol.

Example 1

Based on a standard method authorized by Japanese Society of Chemotherapy (1981), a cashew nut shell liquid and a heat-treated cashew nut shell liquid were measured for the minimum inhibitory concentration (MIC). Preculture was performed using a broth medium for sensitivity measurement (product of NISSUI PHARMACEUTICAL CO., LTD.). An inoculum was adjusted by using physiological saline to about $10^5$ to $10^6$ CFU/ml. A medium for measuring sensitivity (product of NISSUI PHARMACEUTICAL CO., LTD.) was used as a medium for measurement. *Clostridium perfringens* was subjected to an anaerobic culture at 37° C., and determination was made about 20 hours later.

Table 1 shows the results.

TABLE 1

| Strain | Minimum inhibitory concentration (μg/ml) |
|---|---|
| Minimum inhibitory concentration of cashew nut shell liquid | |
| *Clostridium perfringens* W-1 | 6.25 |
| Minimum inhibitory concentration of heat-treated cashew nut shell liquid | |
| *Clostridium perfringens* W-1 | 12.5 |

The cashew nut shell liquid and the heat-treated cashew nut shell liquid are found to have a strong antimicrobial action against *Clostridium perfringens*.

Example 2

500 ml of a GAM broth (product of NISSUI PHARMACEUTICAL CO., LTD.) was prepared in a 1-L Erlenmeyer flask, and the resultant underwent sterilization in an autoclave. After that, each of a cashew nut shell liquid and *Clostridium perfringens* was aseptically administered, and the resultant was subjected to culture under gentle stirring using an incubator at 37° C. under an anaerobic condition. For the test group, 1 g of cashew nut shell liquid was dissolved in 10 ml of dimethylformamide, and 5 ml of the mixture was added in an Erlenmeyer flask. For the control group, 5 ml of dimethylformamide only were added in an Erlenmeyer flask. Preculture of *Clostridium perfringens* was performed in a CW agar medium (product of NISSUI PHARMACEUTICAL CO., LTD.) at 37° C. for 48 hours under an anaerobic condition, and part of the resultant culture was scraped, followed by suspension in sterilized physiological saline. After that, the final concentration of the resultant was adjusted to about $10^6$ CFU/ml. A method of measuring the cell number of *Clostridium perfringens* includes collecting a culture medium aseptically, subjecting the collected culture medium to a 10-fold serial dilution with sterilized physiological saline, inoculating 0.1 ml of a diluted solution at each stage of the dilution to a CW agar medium (product of NISSUI PHARMACEUTICAL CO., LTD.), culturing the resultant at 37° C. for 72 hours under an anaerobic condition to thereby promote the growth of colonies, and then counting the cell numbers in characteristic colonies.

Table 2 shows the results.

TABLE 2

Measurement results of cell number of *Clostridium perfringens*

|  | 0 day of test | Third day of test | Seventh day of test |
|---|---|---|---|
| Control group | $1.1 \times 10^6$ | $8.6 \times 10^6$ | $4.2 \times 10^6$ |
| Cashew nut shell liquid, 0.1% | $1.1 \times 10^6$ | $<10^2$ | $<10^2$ |

The cells of *Clostridium perfringens* were observed throughout the test period in the control group, but the cell number of *Clostridium perfringens* fell to the detection limit or below on the third day and seventh day of the test in the group in which the cashew nut shell liquid had been added. The cashew nut shell liquid is found to have a strong antimicrobial action against *Clostridium perfringens*.

Example 3

Chicks hatched from hatching eggs derived from the broiler breeder (brand name: Chunky) farmed at the first farming site of Hypor Co., Ltd., the chicks having no vaccine history, were preliminarily farmed in an experimental poultry house for 7 days. The chicks were grouped so that each group had 7 chicks. Grouping was done in such a way that there was no difference among groups in the total weight of the chicks at the start of the test. Each of a cashew nut shell liquid and a heat-treated cashew nut shell liquid was added to a feed at 0.5 mass %. The feed was fed to the chicks from after the termination of the preliminary farming until the termination of the test. As feeds, a standard feed for a broiler-fattening earlier stage (SDB No. 1) was fed for testing on chicks from 0 day old to 21 days old, and a standard feed for a broiler-fattening later stage (SDB No. 2) was fed for testing on chicks from 22 days old to 35 days old, both feeds being manufactured by Nippon Formula Feed Manufacturing Co., Ltd. The body weight of the chicks was measured at 8 days old (at the start of the test), 14, 21, 28, and 35 days old. When the farming of the chicks was terminated, 5 chicks per group were chosen at random and sacrificed, and their bellies were opened to collect cecum contents. It should be noted that the cecum contents collected were pooled group by group to be subjected to examination. 1 g of the sample was subjected to a 10-fold serial dilution, and 0.1 ml of the resultant was inoculated on each of 5 sheets of media at each dilution rate. Culture of *Clostridium perfringens* was performed using a CW agar medium (product of NISSUI PHARMACEUTICAL CO., LTD.) at 37° C. for 24 hours under an anaerobic condition. After that, the cell numbers in characteristic colonies were counted.

Table 3 shows the average body weight of the chicks.

TABLE 3

Measurement results of average body weight of chicks (g)

|  | 8 days old | 14 days old | 21 days old | 28 days old | 35 days old |
|---|---|---|---|---|---|
| Control group | 143 | 333 | 619 | 1080 | 1736 |
| Cashew nut shell liquid | 143 | 353 | 690 | 1196 | 1807 |
| Heat-treated cashew nut shell liquid | 143 | 337 | 690 | 1106 | 1786 |

For the chicks fed with a feed to which the cashew nut shell liquid was added at 0.5 mass % and the chicks fed with a feed to which the heat-treated cashew nut shell liquid was added at 0.5 mass %, the average body weight increased compared with the control group. The results show that a cashew nut shell liquid and a heat-treated cashew nut shell liquid have an effect of increasing a body weight.

Table 4 shows the cell number of *Clostridium perfringens* in the cecum contents.

TABLE 4

Measurement results of cell number of enteric bacteria in chicks (CFU/g)

|  | Control group | Cashew nut shell liquid | Heat-treated cashew nut shell liquid |
|---|---|---|---|
| *Clostridium perfringens* | $3.6 \times 10^4$ | $2.3 \times 10^3$ | $4.0 \times 10^2$ |

For the chicks fed with a feed to which the cashew nut shell liquid was added at 0.5 mass %, the cell number of enteric *Clostridium perfringens* dropped to one tenth of that of the control group. Further, in the group treated with the heat-treated cashew nut shell liquid, the cell number of enteric *Clostridium perfringens* dropped to one hundredth of that of the control group. The results corresponded with the results of Examples 1 and 2 in which a cashew nut shell liquid and a heat-treated cashew nut shell liquid have an antimicrobial action against *Clostridium perfringens*.

INDUSTRIAL APPLICABILITY

The present invention provides a feed for prevention and/or therapy of necrotic enteritis, enterotoxemia, and malignant edema caused by the infection of *Clostridium perfringens* and an agent against *Clostridium*.

The controlling agent of the present invention is capable of controlling a disease caused by a *Clostridium* bacterium by administering a cashew nut shell liquid, a heat-treated cashew nut shell liquid, anacardic acid, cardanol, or anacardic acid and cardanol to animals in which the disease caused by a *Clostridium* bacterium is developed, such as livestock and domestic fowls.

The controlling agent of the present invention is capable of killing *Clostridium* bacteria to improve intestinal environment, thereby promoting the growth of an animal.

The invention claimed is:
1. A method of treating livestock suffering a disease caused by a *Clostridium perfringens* bacterium, comprising administering, to the livestock suffering the disease caused by the *Clostridium perfringens* bacterium, an amount of a controlling agent effective to control and/or inhibit growth of the *Clostridium perfringens* bacterium in the livestock and thereby treating the disease, wherein the controlling agent comprises at least one of a cashew nut shell liquid and a heat-treated cashew nut shell liquid, wherein the livestock are in need of treatment for the disease which is caused by the *Clostridium perfringens* bacterium, and wherein the administering includes feeding the livestock a feed comprising the controlling agent.

2. The method of claim 1, wherein the controlling agent comprises at least one of anacardic acid and cardanol.

3. The method of claim 1, wherein the livestock is in need of treatment for at least one disease caused by the *Clostridium perfringens* bacterium selected from the group consisting of necrotic enteritis, enterotoxemia, and malignant edema.

4. The method of claim 1, wherein the livestock is a fowl.

5. The method of claim 1, wherein the livestock is a fowl chick.

6. The method of claim 1, wherein the controlling agent comprises a cashew nut shell liquid containing 55 to 80 mass % of anacardic acid, 5 to 20 mass % of cardanol, and 5 to 30 mass % of cardol.

7. The method of claim 1, wherein the controlling agent comprises a cashew nut shell liquid containing 0 to 10 mass % of anacardic acid, 55 to 80 mass % of cardanol, and 5 to 30 mass % of cardol.

8. The method of claim 1, wherein the administering includes feeding the livestock a feed comprising 0.5 mass % of the cashew nut shell liquid or the heat-treated cashew nut shell liquid.

9. The method of claim 1, wherein said livestock is a cow.

10. The method of claim 1, wherein said livestock is a chicken.

11. The method of claim 1, wherein said livestock is a pig.

12. The method of claim 6, wherein the controlling agent has a minimum inhibitory concentration of 12.5 µg/ml or less according to a standard method authorized by Japanese Society of Chemotherapy (1981).

13. The method of claim 1, wherein the administering includes feeding the livestock a feed comprising 0.001 mass % to 1.0 mass % of the cashew nut shell liquid or the heat-treated cashew nut shell liquid.

14. The method of claim 6, wherein said livestock is a cow.

15. The method of claim 6, wherein said livestock is a chicken.

* * * * *